(12) United States Patent
Taha et al.

(10) Patent No.: US 12,109,380 B1
(45) Date of Patent: Oct. 8, 2024

(54) EXPANDABLE-RETRACTABLE APPARATUS FOR FAST INSERTION OF ECMO AND OTHER CANNULAS (ERIC) VIA RADIAL DILATATION AND METHODS OF MAKING

(71) Applicant: STC Rainforest Innovations, Albuquerque, NM (US)

(72) Inventors: Mahmoud Reda Taha, Albuquerque, NM (US); Eslam Mohamed Soliman, Assiut (EG); Ahmed Reda Taha, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 377 days.

(21) Appl. No.: 17/221,513

(22) Filed: Apr. 2, 2021

Related U.S. Application Data

(60) Provisional application No. 63/004,350, filed on Apr. 2, 2020.

(51) Int. Cl.
    *A61M 29/00*        (2006.01)

(52) U.S. Cl.
    CPC ..... *A61M 29/00* (2013.01); *A61M 2205/0216* (2013.01); *A61M 2205/36* (2013.01)

(58) Field of Classification Search
    CPC .......... A61M 29/00; A61M 2205/0216; A61M 2205/036; A61L 31/022; A61B 17/3203; A61B 17/32037; A61B 17/3417; A61B 17/3421; A61B 17/3423; A61B 17/3431; A61B 17/3439; A61B 2017/00867; A61B 2017/32002; A61B 2017/32007; A61B 2017/32032; A61B 2017/32033; A61B 2017/32035; A61B 2017/32037; A61B 34/30; A61B 34/32; A61B 34/35; A61B 34/37; A61B 34/70; A61B 34/71; A61B 34/73; A61B 34/74; A61B 34/75; A61B 34/76; A61B 34/77; A61B 2034/301; A61B 2034/302; A61B 2034/303; A61B 2034/304; A61B 2034/305; A61B 2034/306; A61B 2034/715; A61B 2034/731; A61B 2034/732; A61B 2034/733; A61B 2034/741; A61B 2034/742; A61F 2/30092; A61F 9/007; A61F 9/0079; A61F 9/00709; A61F 9/00718; A61F 9/00727; A61F 9/00736; A61F 9/00745; A61F 9/00754; A61F 9/00763; A61F 9/00772; A61F 9/00781; A61F 2002/30092
    USPC ........................................................ 606/198
    See application file for complete search history.

(56) References Cited

U.S. PATENT DOCUMENTS

| | | | | |
|---|---|---|---|---|
| 4,411,655 | A * | 10/1983 | Schreck | A61M 25/0662 604/165.01 |
| 5,035,694 | A * | 7/1991 | Kasprzyk | A61M 25/104 604/95.05 |
| 2002/0142119 | A1 * | 10/2002 | Seward | A61L 29/126 428/371 |
| 2007/0142907 | A1 * | 6/2007 | Moaddeb | A61F 2/2469 623/2.37 |
| 2013/0296885 | A1 * | 11/2013 | Desai | A61B 17/3417 606/130 |
| 2019/0175872 | A1 * | 6/2019 | Coker | A61B 8/481 |

(Continued)

*Primary Examiner* — Kankindi Rwego
(74) *Attorney, Agent, or Firm* — Keith Vogt, Ltd.; Keith A. Vogt

(57) ABSTRACT

A dilation system comprising a plurality of springs axially disposed in an elastic tube.

11 Claims, 4 Drawing Sheets

(56) References Cited

U.S. PATENT DOCUMENTS

2020/0281612 A1\* 9/2020 Kelly ................... A61B 17/221
2020/0353226 A1\* 11/2020 Keating ........... A61B 17/12136

\* cited by examiner

EXPANDABLE-RETRACTABLE APPARATUS FOR FAST INSERTION OF ECMO AND OTHER CANNULAS (ERIC) VIA RADIAL DILATATION AND METHODS OF MAKING

RELATED APPLICATIONS

This application claims priority to U.S. Provisional Application No. 63/004,350, filed on Apr. 2, 2020, which is incorporated herein in its entirety.

STATEMENT REGARDING FEDERALLY SPONSORED RESEARCH & DEVELOPMENT

Not applicable.

INCORPORATION BY REFERENCE OF MATERIAL SUBMITTED ON A COMPACT DISC

Not applicable.

BACKGROUND OF THE INVENTION

Percutaneous insertion of vascular cannulas requires dilatation to achieve the puncture site required diameter to pass the vascular cannula. The current practice is to use an axial dilation technique via serial axial dilators with upgraded diameters. This technique is typically required to insert large cannulas such as extracorporeal membrane oxygenation cannula (ECMO) cannulation either in the internal jugular or femoral sites.

The main disadvantages of the current technology and devices may include relatively long operation time consumption and high manpower demand for an operation that requires more than one operator. Additionally, hazards created by axial dilation may include: (1) injuring vascular structure; (2) potential rupture of the vessels distal to the insertion point due to the force applied to the dilator to pass the skin and the soft tissue; and (3) blood loss during the change from one size dilator to another

BRIEF SUMMARY OF THE INVENTION

In one embodiment, the present invention provides a system, apparatus, device, and methods that avoid the limitations and potential risks of axial serial dilators.

In other embodiments, the present invention concerns a system, apparatus, device, and method that provide a new technology for Expandable-Retractable single radial dilator for fast Insertion of ECMO and other cannulas.

In other embodiments, the present invention concerns a system, apparatus, device, and method that provide an expandable-retractable single radial dilator (ERIC) which may be a cylindrical device with an initial guidewire diameter while allowing fast, yet rate controlled, radial dilation of soft tissues to enable loading the cannulas and withdrawing the device.

In other embodiments, the present invention concerns a system, apparatus, device, and method that provide graded longitudinal radial expansion to enable controlled dilation of subcutaneous tissues and the entry site (e.g. vascular).

In other embodiments, the present invention concerns a system, apparatus, device, and method that utilize shape memory alloy technology in a unique manner such that rate controlled graded radial dilation and retraction is accomplished.

In other embodiments, the present invention concerns a system, apparatus, device, and method that provide radial expansion to a pre-determined diameter and retraction to an initial diameter to allow loading of cannulas and their withdrawal.

In other embodiments, the present invention concerns a system, apparatus, device, and method that reduce the risk of vessel rupture, injury, or blood loss.

In other embodiments, the present invention concerns a system, apparatus, device, and method that facilitate fast insertion of different size cannulas less invasively with the use of a single dilator.

In other embodiments, the present invention concerns a system, apparatus, device, and method that reduce the operation time required for cannulation and minimizing bleeding incidents that can happen during changing multiple serial dilators.

In other embodiments, the present invention concerns a system, apparatus, device, and method that enable a single operator to easily introduce and load a cannula.

In other embodiments, the present invention concerns a dilation system, apparatus, device, and method that allow for rate controlled and longitudinally graded radial dilation of the insertion site including the subcutaneous tissues and the entry site (e.g. vascular).

In other embodiments, the present invention concerns a system, apparatus, device, and method that provide an expandable-retractable single radial dilator that enables fast, yet rate controlled, radial dilation of soft tissues to enable loading the cannulas and withdrawing the device.

In other embodiments, the present invention concerns a system, apparatus, device, and method that perform radial dilation while minimizing the force used for insertion and dilatation by axial dilators thus minimizing vascular injuries through and distal to the insertion site.

In other embodiments, the present invention concerns a system, apparatus, device, and method that allow for the insertion of large-size cannulas during out-of-hospital cardiac arrest and ECPR as well as in-hospital ECMO cannulation.

In other embodiments, the present invention concerns a system, apparatus, device, and method that allow rate-controlled graded radial expansion and retraction using shape memory alloy components.

In other embodiments, the present invention concerns a system, apparatus, device, and method that provide an engineered combination of shape memory alloy types and components to allow expandable/retractable longitudinally graded radial dilation by controlling temperature, stiffness, and/or stress.

In other embodiments, the present invention concerns an expandable-retractable apparatus that allows the fast insertion of large cannulas via radial dilatation.

In other embodiments, the present invention concerns a low-invasive approach to the insertion of large cannulas.

In other embodiments, the present invention concerns a method that allows a short time-period to restore circulation and perfusion during extracorporeal membrane oxygenation (ECPR) where time is critical to limit brain damage.

In other embodiments, the present invention concerns an apparatus and device and a non-complex procedure with minimal blood loss and limited tissue injuries.

In other embodiments, the present invention concerns an apparatus and device that can be used in numerous other applications that need rate-controlled radial dilation (e.g. tracheostomy, PEG tube insertion, etc.).

In other embodiments, the present invention concerns a system, apparatus, device, and method that are not redistricted to medical applications but can be used in other fields where rate-controlled graded radial dilation is required.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

DETAILED DESCRIPTION OF THE INVENTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure, or system. Further, the terms and phrases used herein are not intended to be limiting, but rather to provide an understandable description of the invention.

Figure 1:
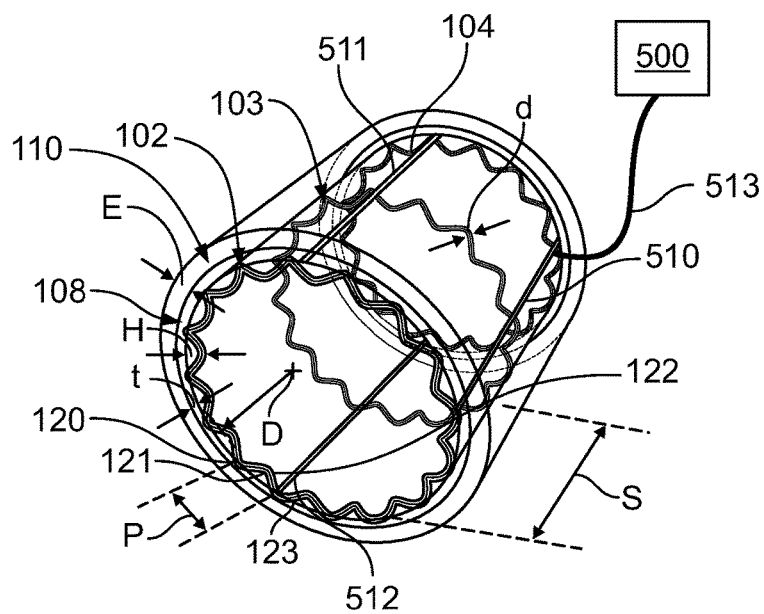
FIG. 1 illustrates a first embodiment of the present invention.

A preferred dilation system of the present invention is shown in FIGS. 1-4. As shown, the dilation system may include dilator 100 which, in turn, may consist of shape memory alloys (SMA) springs 102-104 arranged axially within an SMA tube 108. Different types of shape memory alloys can be used to achieve a desired and gradual dilation performance. In FIG. 1 the following geometrical design parameters are further referenced: P: Spring pitch, D: Spring diameter, H: Spring Height, S: Spacing between Springs, d: Spring size, t: Tube thickness and E: Thickness of polymer enclosure. The geometrical parameters and material types can be designed to suit various medical applications, various sustained pressure levels, and varying gradual dilations.

Dilator 100 is configured to expand and retract based on temperature and/or stress conditions. Springs 102-104 utilize shape memory (two-phase material) effect to increase the diameter when the temperature raises by recovering their original/parent shape. Tube 108 is adapted to retract springs 102-104 when the temperature drops by compressing the springs mainly via an elastic effect.

As is further shown, the dilation system of the present invention may also include electrical power supply 500 connected to heating elements 510-512. In a preferred embodiment, wire 513 is connected to heating elements 510-512. When electrical current is supplied, the temperature of heating elements 510-512 increases. Heating elements 510-512 may be disposed along the outer circumference of dilator 100 and embedded in tube 108. The heating elements are arranged to extend axially along the device and may be interconnected. While rectangular bars are illustrated, the heating elements may have other configurations designed to adequately heat the springs such as linear segments, non-linear segments and segments that include linear and non-linear sections. The springs themselves may also be electrically connected and function as heating elements.

Tube 108 may also be configured to transfer heat to the springs and to ensure stability rate controlled graded radial deformations during dilation and retraction.

The number of components and their composition, as well as their distribution along the device, is determined by design to satisfy performance requirements. Tubing 108 may be enclosed in a polymer 110 or other material enclosure to prevent leakage and act as an insulator for heat and electric current.

Figure 2:
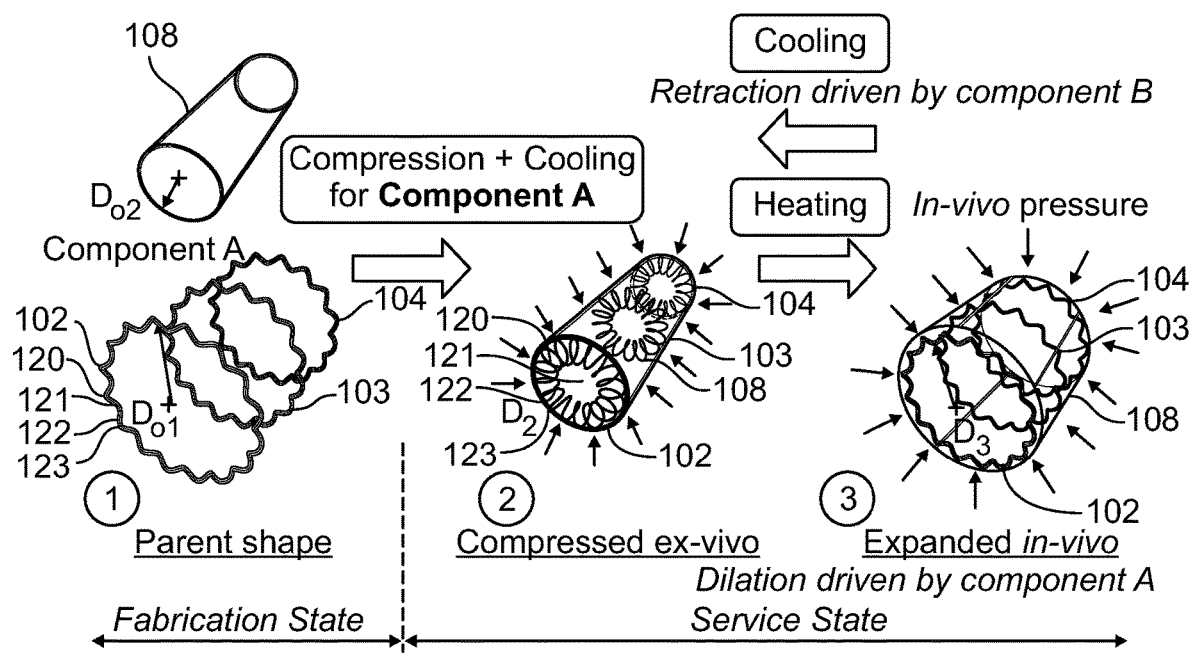
FIG. 2 is a schematic of the embodiment shown in FIG. 1.
Figure 3:
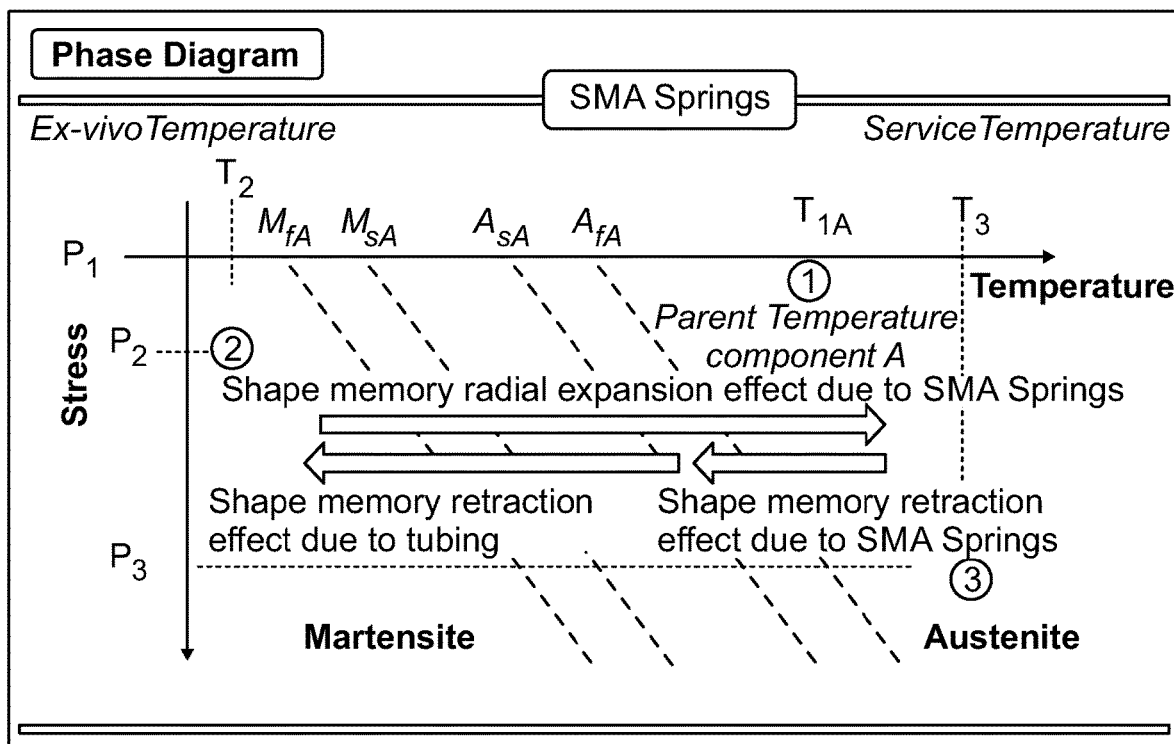
FIGS. 3 and 4 are process flowcharts for the embodiment shown in FIG. 1.
Figure 4:
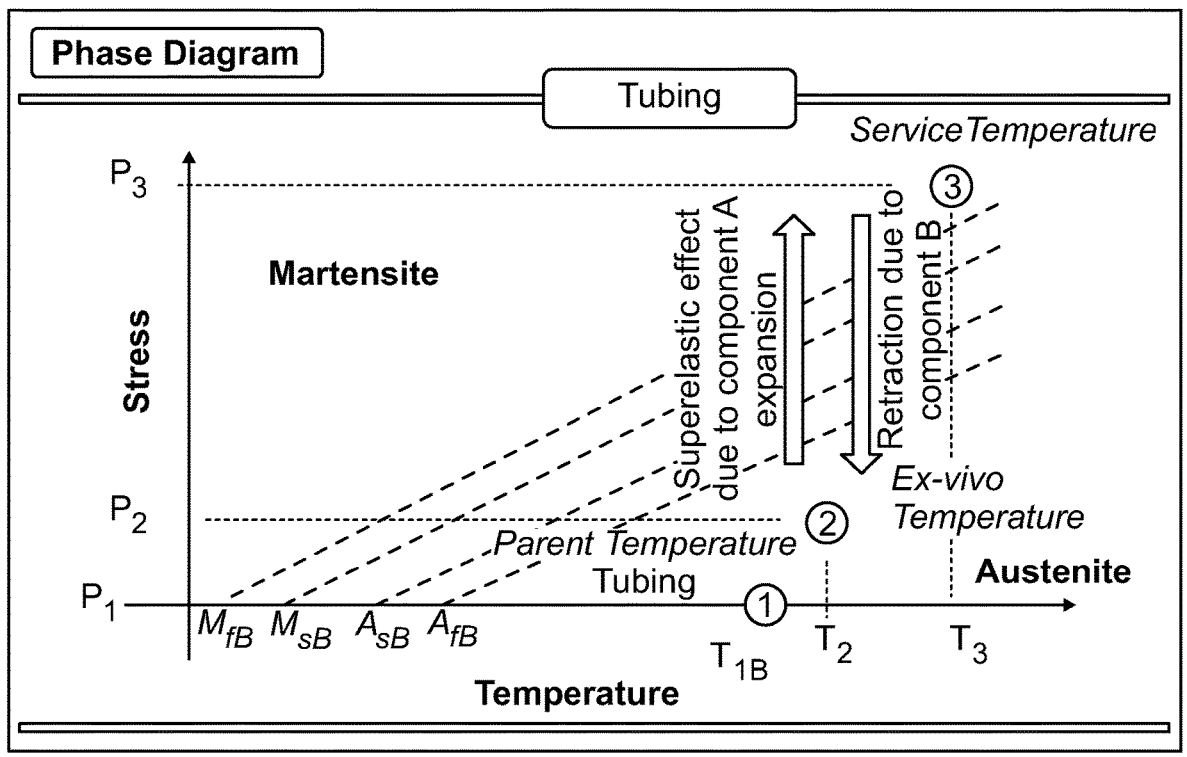

As shown in FIG. 2, dilator 100 may have three stages consisting of a parent stage 1, compressed stage 2, and dilated stage 3, which will be discussed below. Also, phase diagrams for the embodiments of the present invention are provided in FIGS. 3 and 4 and concern the parent stage 1, compressed stage 2, and dilated stage 3.

Parent Stage

The parent stage is a fabrication state where springs 102-104 are at a stress-free condition ($P_1 \approx 0$) and are fabricated in an Austenite state at a temperature $T_{1A}$ that is higher than Austenite final temperature $A_{fA}$ ($T_{1A} > A_{fA}$) with a diameter $D_{01}$. At this stage, springs 102-104 define a first circumference. Tubing 108 is fabricated in Austenite state at a temperature $T_{1B}$ that is higher than Austenite final temperature $A_{fB}$ ($T_{1B} > A_{fB}$) with a diameter $D_{02}$ which is smaller than $D_{01}$.

Compressed Stage

The compressed stage represents ex-vivo service conditions. Springs 102-104 transform to a Martensite state by cooling to low temperature ($T_2 < M_{fA}$) and are compressed to a diameter ($D_2 < D_{01}$) under the external pressure $P_2$ exerted by tubing 108. At this stage, springs 102-104 define a second circumference which is smaller than the first circumference. Tubing 108 remains in an Austenite state and slightly expands to a diameter ($D_2 > D_{02}$) at a temperature ($T_2 \geq T_{1B}$) under limited internal pressure $P_2$ due to the springs. External pressure may also be applied to the system at this stage to simulate in-vivo pressure depending on the medical application, the type and stiffness of the tissue penetrated before the insertion and dilation process takes place.

Dilated Stage

The dilated stage represents in-vivo service conditions. By applying heat to springs 102-104, by an electrical connection as discussed above, chemically, or by other means, springs 102-104 are transformed to an Austenite phase by heating to a temperature $T_3$ ($T_3 > A_{fA}$) to recover their parent shape. Springs 102-104 radially expand to a target diameter $D_3$ ($D_2 > D_3 > D_{01}$) creating a third circumference which may be the same as the first circumference, larger than the first circumference, or smaller than the first circumference but larger than the second circumference, under the external pressure of $P_3$ ($P_3 \geq P_2$). The target diameter may vary to suit different medical applications. The target diameter may also vary longitudinally to create desired dilation profiles that suit different medical insertions or tissue stiffness. Graded dilation can also be created using a combination of different types of shape memory alloy springs combined in one tube. Tubing 108 transforms to the Martensite phase due to internal pressure caused by the large radial expansion of springs 102-104. Tubing 108 observes super elastic deformations and expands to a target diameter $D_3$ during phase transformation.

Second Compressed Stage

Dilator 100 can be retracted by cooling to temperature ($T_2<M_{f4}$). Tubing 108 transforms back to Austenite due to cooling and retracts the system by compressing springs 102-104 to a diameter $D_2$. Springs 102-104 transform back to the Martensite state due to cooling and external pressure from tubing 108.

In another preferred embodiment as shown in FIG. 2, to create springs with the ability to transition between circumferences of various sizes by changing the number or type of shape memory alloys, the pitch P, and height H, spring 102 includes one or more points such as points 120 and 123 connected by segments 121 and 122. The points are located around the circumference of a spring. When spring 102 is in its first circumference, the distance or between points 120 and 123 or pitch P is greater than when spring 102 is in its second circumference.

To allow points 120 and 123 to move towards one another to decrease the pitch when transitioning from the dilated stage to the compressed stage, segments 121 and 122 are directed radially towards the center of spring 102. Portions of the springs need to be directed inwardly or away from the circumference to create the smaller spring circumference, Also, when the spring pitch P increases, spring height H decreases. Conversely, when pitch P decreases, height H increases. Lastly, as shown in FIG. 2, in certain embodiments, the plurality of segments such as segments 121 and 122 form one or more loops when directed inwardly when in the compressed stage and connected curved paths when in the dilated stage.

Figure 5:
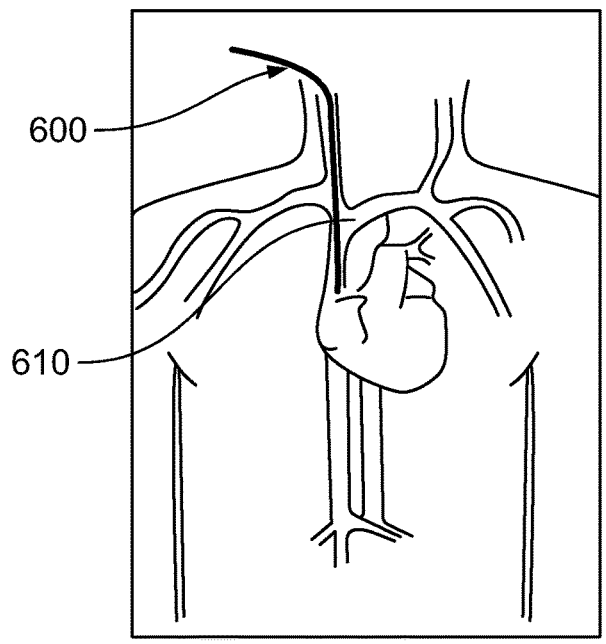
FIGS. 5, 6, 7, 8 and 9 illustrate one method of using the embodiment shown in FIG. 1.
Figure 6:
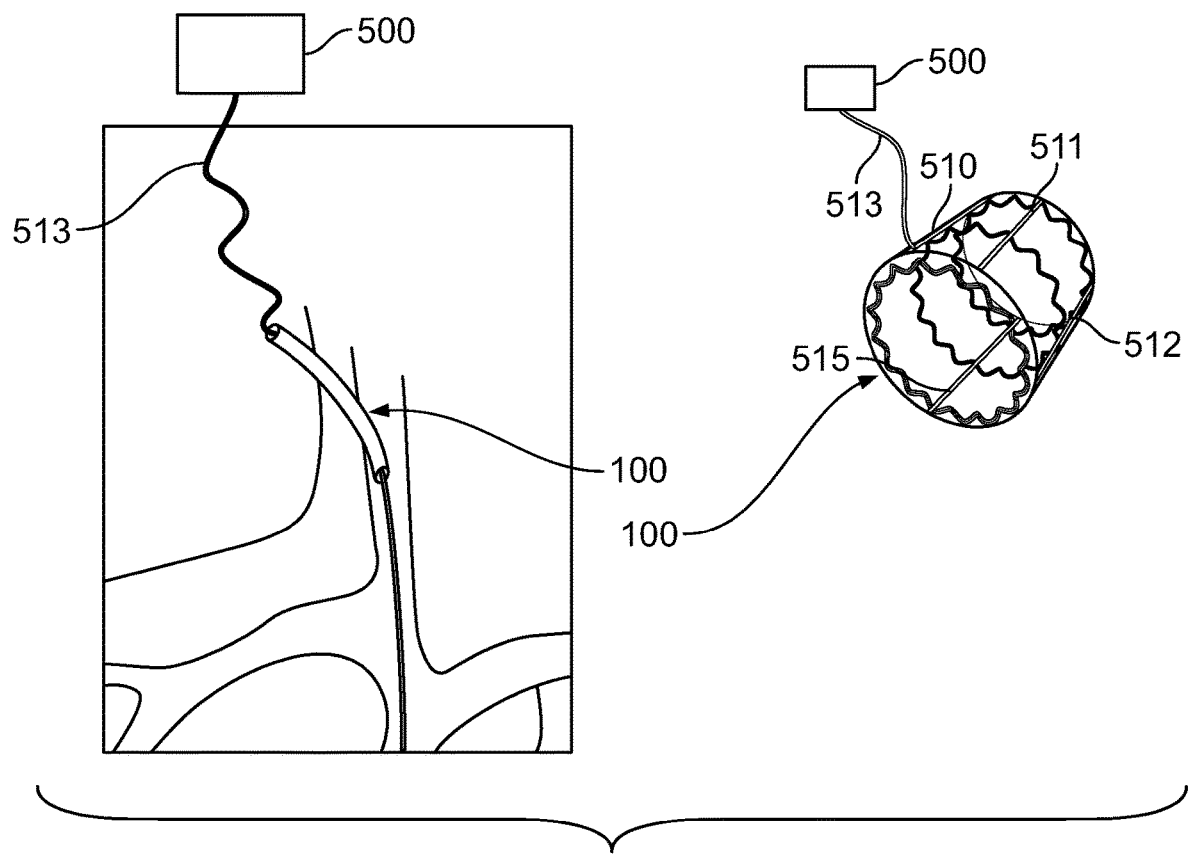
Figure 7:
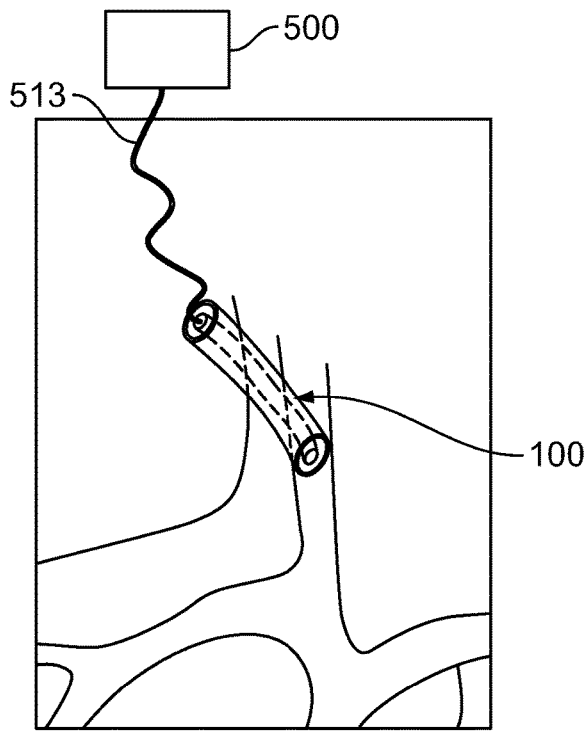

FIGS. 5-9 illustrate one method of using dilator 100 and power supply 500 as a dilation system in connection with a portion of a human vascular network. As shown in FIG. 5, guidewire 600 is first inserted into vascular portion 610. As shown in FIG. 6, dilator 100 is slid at its small diameter (5 French and in the compressed stage) on guidewire 600 to be placed inside section 610 which may be a vein, artery, or tissue. As shown in FIGS. 6 and 7, dilator 100 is connected to an electrical current via power supply 500 and wire 513 to heat thermal elements 510-512 and 515 which may be bars to a target temperature (within body temperature) to expand dilator 100 of the dilation system.

Figure 8:
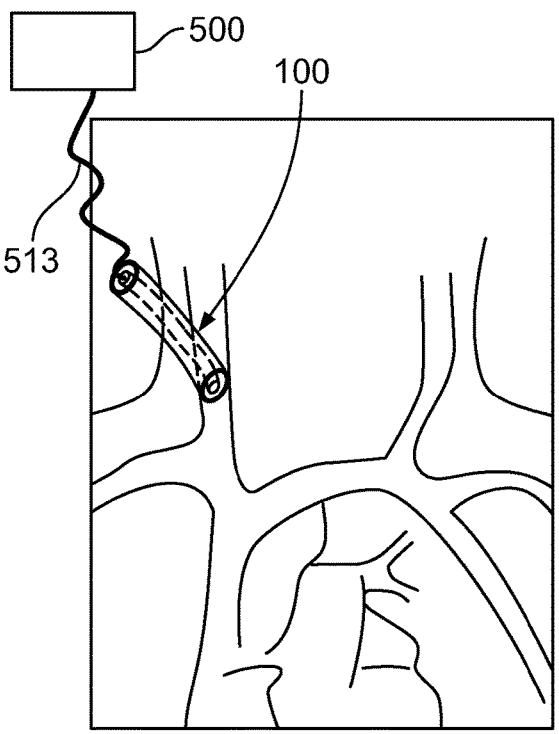

As shown in FIG. 8, dilator 100 is expanded to an increased diameter from (5 French) to (36 French) using an electrical current. Electrical current can be used to heat selected springs to obtain a desired dilation profile. In other embodiments, the electrical current may be applied in a manner that produces a graded or gradual expansion. This may be achieved by selective heating such that current is applied to some elements 102 and 103 at first then others 104 later in time. In yet other embodiments, the current may also be gradually increased. In yet other embodiments, the heating elements for different durations of time. The ability to control the rate of heating as produces a specific dilatation at a specific time period when the system transitions from the compressed stage to the dilated stage.

To achieve a grade or gradual retraction, the reverse of the above may be performed. Heating may be selectively removed such that current is removed from some elements 102 and 103 at first then others 104 later in time. In yet other embodiments, the current may also be gradually decreased. The ability to control the rate of cooling produces a specific dilatation at a specific time period when the system transitions from the dilated stage to the compressed stage.

Selective heating and selective cooling produces a graded dilation or retraction along the device. This creates the ability to control the stiffness/pressure of the device to be able to use it in different locations.

Figure 9:
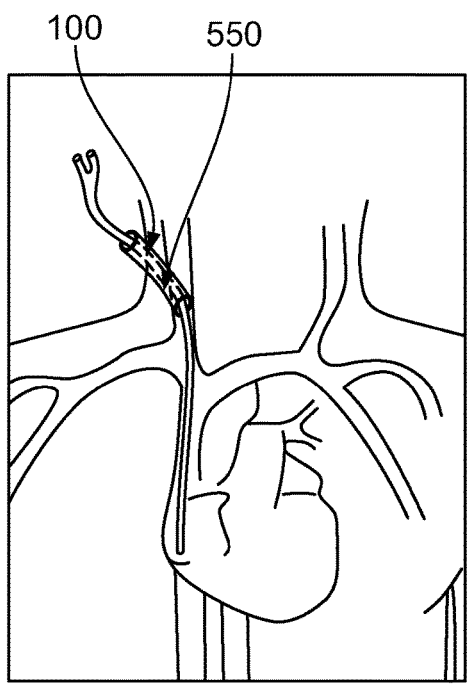

As shown in FIG. 9, cannula 550 is passed through dilator 100 and, thereafter, dilator may be withdrawn by compressing it down to a smaller size. This may be done by the compressive force created by the tubing discussed above. In addition, the current may be reduced or eliminated which also assists in reducing the circumference defined by the springs While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above-described embodiments, methods, and examples, but by all embodiments and methods within the scope and spirit of the disclosure.

What is claimed is:

1. A dilation system comprising:
a plurality of springs axially disposed in a tube, said plurality of springs having an Austenite state having a temperature $T_{1A}$, an Austenite final temperature $A_{fA}$ and Martensite state having a temperature $M_{fA}$;
said tube having an Austenite state having a temperature $T_{1B}$, an Austenite final temperature $A_{fB}$ and Martensite state;
said plurality of springs and said tube having a parent stage, compressed stage and dilated stage;
in said parent stage, said plurality of springs are at a temperature $T_{1A}$ that is higher than said Austenite final temperature $A_{fA}$ ($T_{1A}>A_{fA}$) with a spring diameter $D_{01}$;
in said parent stage, each of said plurality of springs define a first circumference;
in said parent stage, said tube is in said Austenite state at a temperature $T_{1B}$ that is higher than said Austenite final temperature $A_{fB}$ ($T_{1B}>A_{fB}$) with a tube diameter $D_{02}$ which is smaller than said spring diameter $D_{01}$;
in said compressed stage, said plurality of springs transform to said Martensite state by having a temperature lower than said Martensite temperature $M_{fA}$ and are compressed to a diameter $D_2$ under external pressure $P_2$ created by said tube;
in said compressed stage, each of said plurality of springs define a second circumference which is smaller than said first circumference;
in said dilated stage, said plurality of springs transform to said Austenite stage by having a temperature $T_3$ greater than said Austenite final temperature $A_{fA}$;
in said dilated stage, said plurality of springs radially expand to a third circumference which may be the same as said first circumference, larger than said first circumference, or smaller than said first circumference but larger than said second circumference due to pressure exerted by said tube;
in said dilated stage, said tube transforms to said Martensite state due to internal pressure caused by said radial expansion of said plurality of springs and
wherein spring height increases when transitioning from said dilated stage to said compressed stage.

2. The dilation system of claim 1 wherein said plurality of springs include connected curved segments when in said dilated stage and said segments form loops when in said compressed stage.

3. The dilation system of claim 1 further including a power supply electrically connected to a plurality of heating elements.

4. The dilation system of claim 3 wherein said plurality of springs are said plurality of heating elements.

5. The dilation system of claim 3 wherein said heating elements are selectively cooled to produce a specific dilatation at a specific time period when the system transitions from the dilated stage to the compressed stage.

6. The dilation system of claim 5 wherein said heating elements are selectively cooling by reducing the current applied to said heating elements for different durations of time.

7. The dilation system of claim 5 wherein said heating elements are selectively cooling by gradually reducing the current applied to said heating elements.

8. The dilation system of claim 3 wherein said heating elements are selectively heated to produce a specific dilatation at a specific time period when the system transitions from the compressed stage to the dilated stage.

9. The dilation system of claim 8 wherein said heating elements are selectively heated by heating said heating elements for different durations of time.

10. The dilation system of claim 8 wherein said heating elements are selectively heated by heating said heating elements with different amounts of current.

11. The dilation system of claim 8 wherein said heating elements are selectively heated by heating said heating elements with different amounts of current.

\* \* \* \* \*